United States Patent [19]
Gemma

[11] Patent Number: 6,138,440
[45] Date of Patent: Oct. 31, 2000

[54] SURGICAL SUTURE RETAINER PACKAGE

[75] Inventor: Edward A. Gemma, Milford, Conn.

[73] Assignee: United States Surgical Corporation, Norwalk, Conn.

[21] Appl. No.: 09/260,111

[22] Filed: Mar. 2, 1999

Related U.S. Application Data

[60] Provisional application No. 60/077,293, Mar. 6, 1998.
[51] Int. Cl.[7] .......................... B65B 63/04; B65B 55/02; A61B 17/06
[52] U.S. Cl. ............................ 53/430; 53/425; 206/63.3
[58] Field of Search .......................... 53/430, 116, 425, 53/449, 470–472; 206/63.3

[56] References Cited

U.S. PATENT DOCUMENTS

| | | | |
|---|---|---|---|
| 3,728,839 | 4/1973 | Glick | 53/449 |
| 3,815,315 | 6/1974 | Glick | 53/449 |
| 5,121,836 | 6/1992 | Brown et al. | 206/63.3 |
| 5,228,565 | 7/1993 | Sinn | 53/430 |
| 5,249,671 | 10/1993 | Sinn | 206/63.3 |
| 5,359,831 | 11/1994 | Brown et al. | 53/430 |
| 5,439,102 | 8/1995 | Brown et al. | 206/63.3 |
| 5,461,844 | 10/1995 | Brown | 53/430 |
| 5,494,154 | 2/1996 | Ainsworth et al. | 206/63.3 |
| 5,566,821 | 10/1996 | Brown et al. | 206/63.3 |

*Primary Examiner*—Brian L. Johnson
*Assistant Examiner*—Matthew Luby

[57] ABSTRACT

A method for loading a needle-suture combination into a package includes the steps of positioning the needle in the base portion of the package, and laying down a major portion of the suture between two V-shaped guides so as to preferably form a suture coil having generally figure 8 shaped loops. Winding pins can be used to facilitate the winding of the suture into a coiled configuration. The cover portion of the package is attached to the base by snap lock engagement. The loaded package can be thereafter be sealed in an envelope and sterilized.

20 Claims, 7 Drawing Sheets

SURGICAL SUTURE RETAINER PACKAGE

This application claims priority to U.S. Ser. No. 60/077,293 filed on Mar. 6, 1998.

BACKGROUND

1. Technical Field

The present disclosure relates to a package for retaining, storing, and dispensing a surgical needle-suture combination.

2. Background of Related Art

Packages for retaining armed sutures, i.e., sutures with surgical needles attached, are known. For example, U.S. Pat. No. 5,566,821 to Brown et al. discloses a surgical suture retainer which retains the suture in an epitrochoidal, or hourglass configuration. One embodiment includes an insert member mounted to one of several foldable connected panels of the suture retainer. The insert member preferably has first and second wings which fold over to form a suture retaining pocket. The suture is held in a looped configuration having an hourglass shape. Another embodiment employs tabs cut from one of the panels to retain the suture in the hourglass shape. Yet another embodiment employs a cover sheet bonded to a base panel, wherein bonding areas are located to maintain the suture loop in an hourglass shape.

U.S. Pat. No. 5,439,102 to Brown et al. discloses a moisture impervious package for surgical elements such as retainers having suture-needle assemblies positioned thereon. The package is provided with a top wall of moisture impervious material having an access opening die cut into the wall over which a closure flap secured by a peripheral heat seal to fully enclose the access opening. The top wall is then positioned over a bottom wall of moisture impervious material whereby a retainer having the suture needle assemblies is positioned therebetween. A peripheral heat seal then secures the top wall to the bottom wall to form the package.

U.S. Pat. No. 5,359,831 to Brown et al. discloses a molded suture retainer for retaining and storing surgical sutures in a manner which reduces kinking and bending of the sutures. The retainer is characterized by a wide spiraling oval passageway with minimal convolutions covered by a cover sheet. The length of the passageway is preferably proportional to ⅓ to ½ the overall length of the suture to be retained therein. Recesses are provided for receiving package stabilizing agents and/or needle parks.

SUMMARY

A method is provided herein for loading a needle-suture combination into a package. The method comprises: (a) providing at least one needle-suture combination; (b) providing a needle-suture retaining package which includes a cover, and a base which is attachable to the cover so as to define an enclosure volume, the base having first and second V-shaped ridges, each V-shaped ridge having a vertex portion, the vertex portion of the first V-shaped ridge being in opposing relation to the vertex portion of the second V-shaped ridge so as to define a constricted space therebetween; (c) positioning the needle in the base; (d) laying a major portion of the suture down between the first and second V-shaped ridges, preferably so as to form a suture coil having generally figure 8 shaped loops; and (e) attaching the cover to the base.

BRIEF DESCRIPTION OF THE DRAWINGS

Various embodiments are described below with reference to the drawings wherein.

DETAILED DESCRIPTION OF THE PREFERRED EMBODIMENTS

As used herein the terms "distal" and "proximal", "above" and "below", "up" and "down", "left" and "right" and similar such terms are used relative to each other and not to an external fixed frame of reference.

Figure 1:
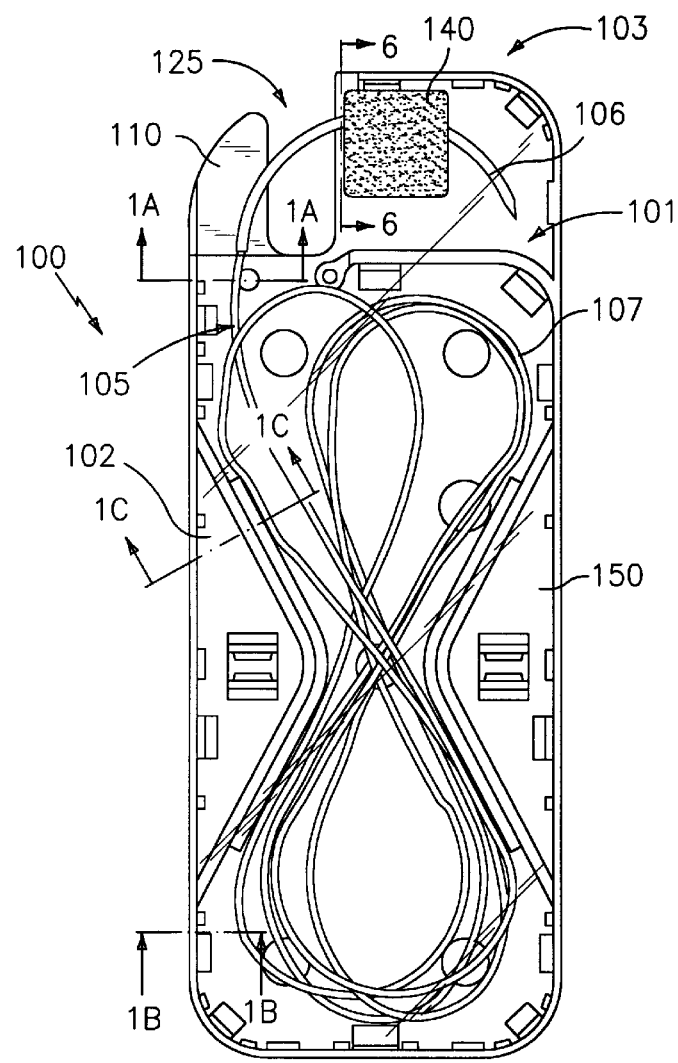
FIG. 1 is a top plan view of the suture retainer package with an armed suture stored therein.
Figure 2:
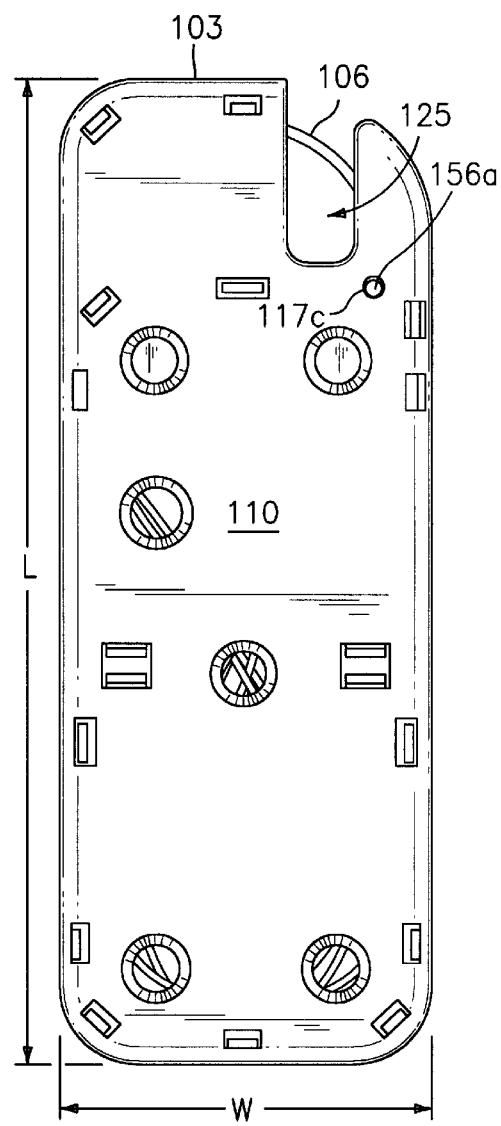
FIG. 2 is a bottom view of the suture retainer package with an armed suture stored therein.

Referring to FIGS. 1 and 2, suture retainer package 100 is container for holding and dispensing a needle-suture combination 105, which includes a surgical needle 106 to which suture 107 is attached. Needle 106 is typically curved into an arcuate shape and is typically fabricated from stainless steel. Suture 107 can be monofilament or multifilament, and can be bioabsorbable or non-bioabsorbable. Typical non-bioabsorbable materials from which sutures can be fabricated include nylon and polypropylene. Bioabsorbable materials can be natural materials such as catgut or collagen, or synthetic materials such as polymers of glycolide, lactide, p-dioxanone, ε-caprolactone, trimethylene carbonate, and physical and chemical combinations thereof. Needle and suture diameter can vary according to the intended use. For example, typical sizes for sutures can range from USP Size 12-0 (about 0.001 to about 0.009 mm) to USP Size 10 (about 1.200 to about 1.299 mm). As can be seen from FIG. 1, the suture is stored in the suture retainer package 100 in a looped coil configuration, the loops being shaped approximately as a figure 8. The needle 106 is positioned at one end of the suture retainer package 100 and is held in place by a foam pad 140, as discussed below.

The suture retainer package 100 is generally flat and rectangular in shape and includes a base 110 and a cover 150. Generally the suture retainer package 100 can have a length L ranging from about 3.30 inches to about 4.00 inches and width W ranging from about 1.25 inches to about 1.65 inches. Distal end 103 of the suture retainer package 100 provides an exit for the needled suture, as discussed below.

Base 110 and cover 150 can be fabricated from the same or different synthetic polymers selected from, for example, polypropylene, HDPE, and the like. The synthetic polymer should have sufficient strength, flexibility, and resiliency for the purposes described below and should be medically compatible with the intended purpose of storing surgical needles and sutures. Cover 150 is preferably transparent to allow visualization of the contents of the suture retainer package 100. Cover 150 or base 110 may optionally have attached thereto a sheet of paper or other material (not shown) having indicia printed thereon for identification of the contents of the suture retainer package 100.

Figure 1A:
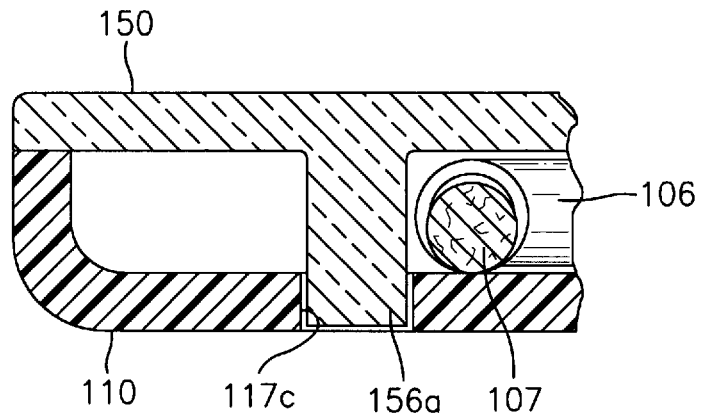
FIG. 1A is a sectional view taken along line 1A—1A in FIG. 1.
Figure 1B:
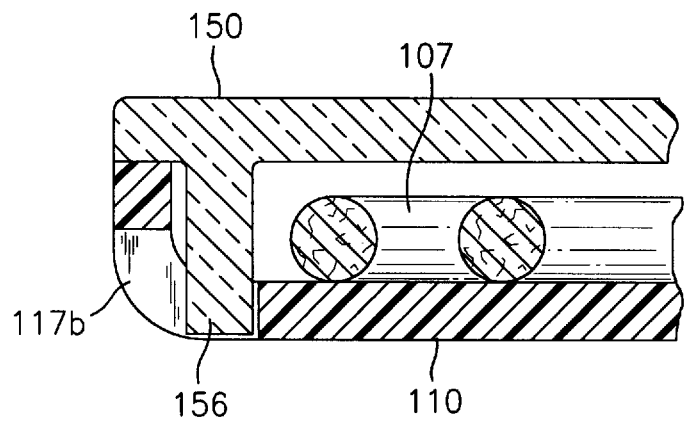
FIG. 1B is a sectional view taken along line 1B—1B in FIG. 1.
Figure 3:
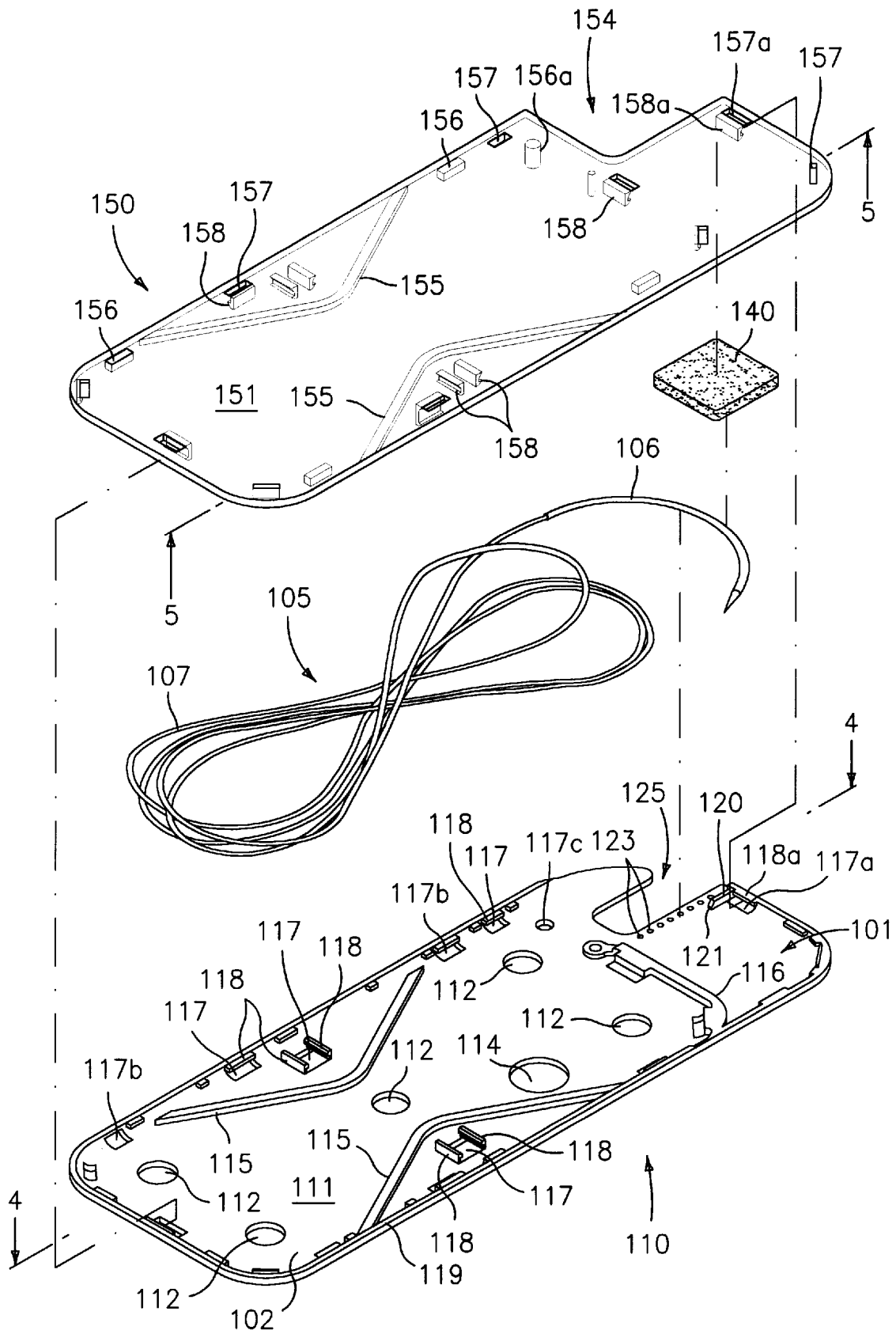
FIG. 3 is an exploded perspective view of the suture retainer package with an armed suture stored therein.
Figure 4A:
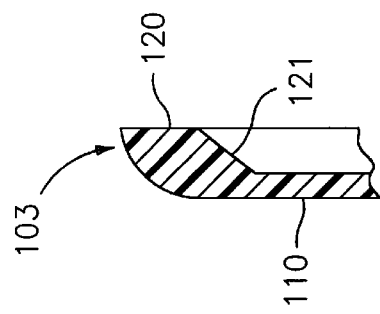
FIG. 4a is a detailed sectional side view of the camming wall of the base.
Figure 4:
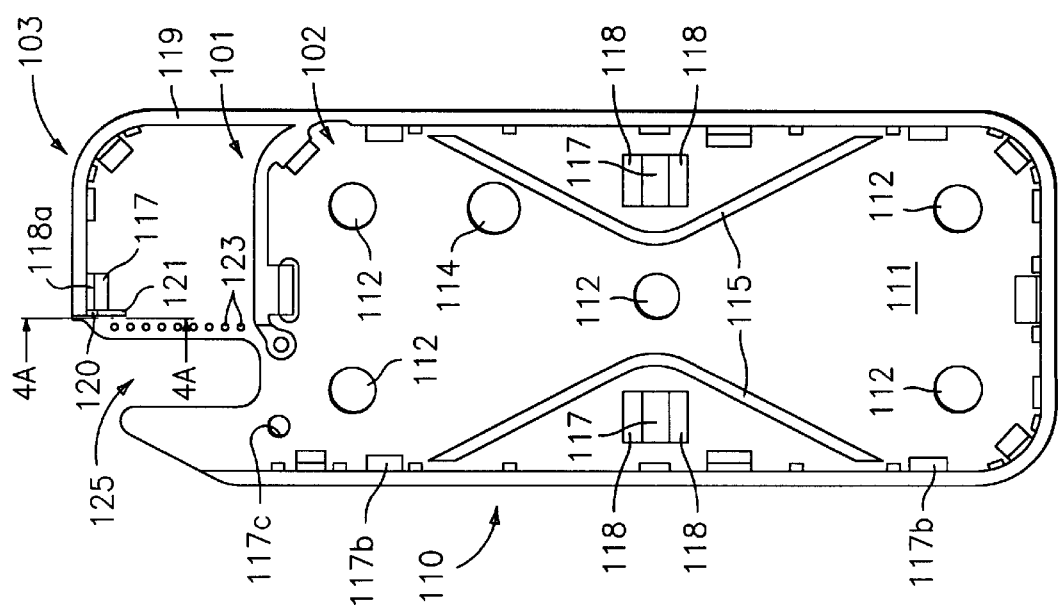
FIG. 4. is a top plan view of the base.

Referring additionally now to FIGS. 3, 4, and 4a, base 110 is an integral single piece body 111 having a plurality of winding pin apertures 112, a central orientation pin aperture 113, and an asymmetrically positioned aperture 114 for reception of the tail end of the suture. V-shaped ridges 115, in conjunction with corresponding V-shaped ridges 155 of the cover 150, serve as guides to constrict the center of the suture loop to maintain the suture loops in the desired figure 8 configuration. As can be seen from FIGS. 1, 3, and 4, each of the two V-shaped ridges 115 has a vertex portion in opposing relationship to the vertex portion of the other V-shaped ridge so as to define a constricted space therebetween. Base 110 includes a plurality of slots 117 and projections 118 which serve as catches. Slots 117 are adapted to receive latches 158 of the cover 150; catches 118 are adapted to engage corresponding latches 158 to lock together the cover 150 and base 110 with snap lock engagements. Additionally, as shown in FIG. 1B, slots 117b in the base are adapted to engage bosses 156, which project downwardly from the cover 150. The bosses 156 are flat, plate like projections which serve as baffles to prevent the suture from getting engaged on or caught in the junction between cover 150 and base 110. As shown in FIG. 1A, in the vicinity of distal exit end 103 of the package the baffle is preferably a depending cylindrical boss 156a which engages a circular slot 117c to prevent snagging of the suture upon its withdrawal from package 100. Peripheral ridge 119 extends upward around the edge of the base 110 to define an enclosure volume in which the needle-suture combination 105 is stored. Ridge 116 serves as a wall to divide the enclosure volume into a needle storage compartment 101 and a suture storage compartment 102.

In the vicinity of the distal left corner the base includes a lengthwise extending notch 125 across which needle 106 extends. Notch 125 permits the needle to be grasped by a suitable grasping instrument for removal from the suture retainer package 100.

Base 110 includes a longitudinally oriented camming wall 120 extending from end 103 of the suture retainer package 100 and having a proximal inclined camming surface 121. Camming wall 120 is positioned adjacent the left side of slot 117a and catch 118a. Camming surface 121 is adapted to be slidingly engaged by needle 106 as explained below. A longitudinal row of spaced apart indexing studs 123 is positioned along the right side of notch 125. Studs 123 permit the stabilized positioning of the needle 106 at discrete spaced apart intervals in the needle storage compartment 101.

Figure 1C:
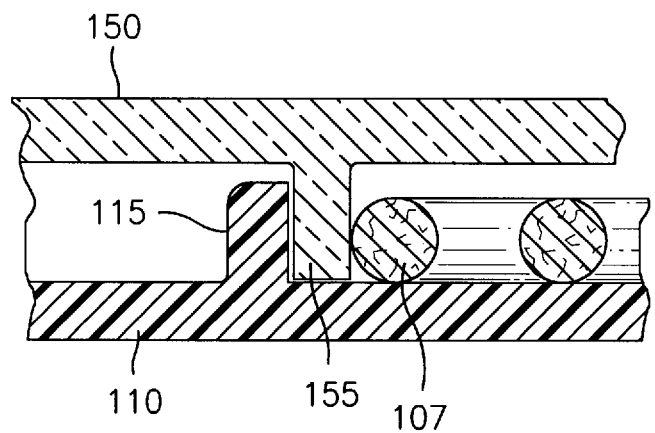
FIG. 1C is a sectional view taken along line 1C—1C in FIG. 1.
Figure 5A:
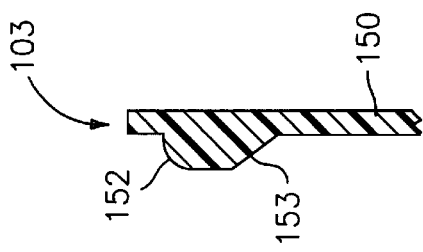
FIG. 5a is a detailed sectional side view of the camming wall of the cover.
Figure 5:
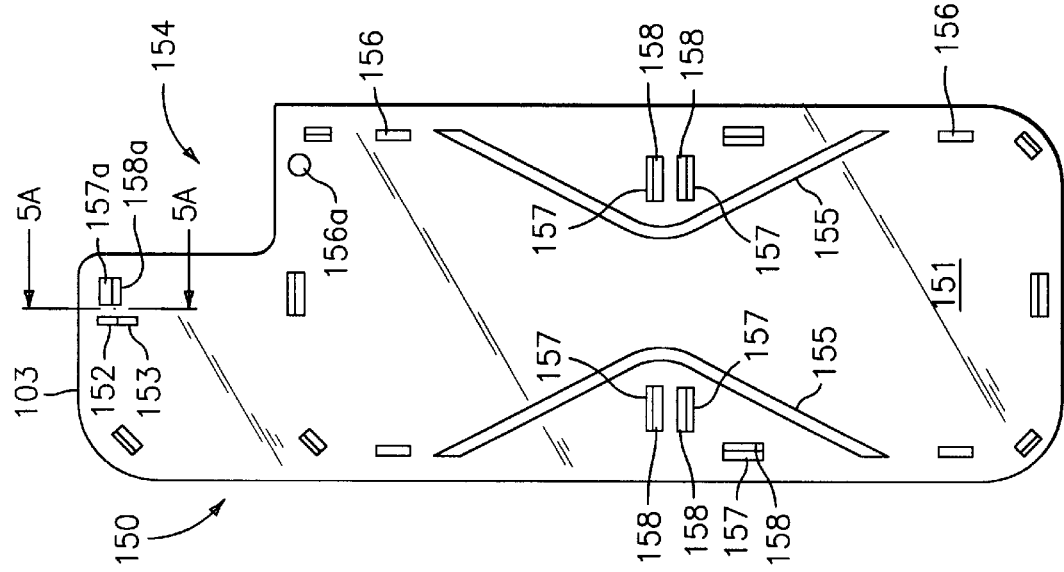
FIG. 5 is a bottom view of the cover.

Referring now to FIGS. 1, 3, and 5, cover 150 includes an integral single piece body 151 having a cutaway portion 154 at the distal left corner. Downward projecting latches 158 are adapted to engage corresponding slots 117 and/or catches 118 in the base. Particularly, latch 158a is adapted to engage slot 117a and catch 118a in the base. Referring to FIG. 1C, cover 150 further includes V-shaped ridges 155 which, when the cover 150 and base 110 are assembled, are adjacent to corresponding ridges 115 in the base to constrict the center of the suture loop as mentioned above. The V-shaped ridges 115 and 155 cooperate to prevent the suture from getting caught or snagged in the snap lock engagements. Foam pad 140 can be attached to the underside of cover 150, for example by adhesive, and is positioned to contact needle 106. Foam pad 140 can preferably an open celled polymeric material such as, for example, polyurethane. Foam pad 140 helps to keep needle 106 stably positioned in the suture retainer package 100 until intentionally removed by the surgeon. Alternatively, foam pad 140 can be positioned on base 110 and needle 106 can be secured to the foam pad 140 by, for example, insertion into the foam pad by piercing or being positioned within a slot in the foam pad.

Referring now to FIGS. 1, 3, 5, and 5a, cover 150 includes a longitudinally oriented camming wall 152 extending from end 103 of the suture retainer package 100 and having a proximal inclined camming surface 153. Camming wall 152 is positioned adjacent the right side of latch 158a and slot 157a. Camming surface 153 is adapted to be slidingly engaged by the needle 106 as explained below.

Figure 6:
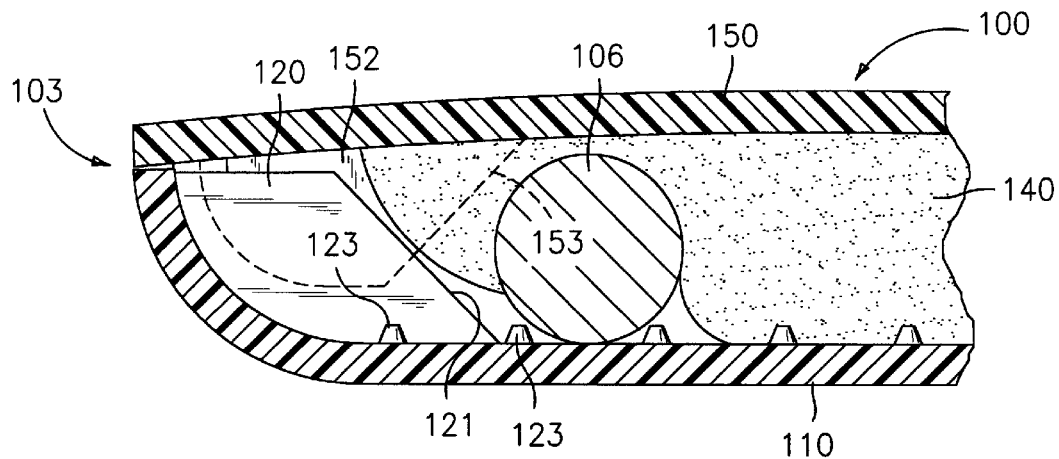
FIGS. 6, 7, and 8 are sectional side views progressively illustrating the removal of a surgical needle from the suture retainer package.

As can be seen now in FIG. 6, needle 106 is secured in a desired storage position within the closed suture retainer package 100 by indexing studs 123 and foam pad 140. The position of the needle along the line of indexing studs can be selected based on, for example, the degree of curvature of the needle. Alternatively, more than one needle-suture combination can be stored in the suture retainer package 100 and multiple needles can be spaced apart in the needle storage chamber 101 at respective indexed locations. Removal of the needle 106 is accomplished by grasping the needle with an appropriate instrument at the portion of the needle extending across notch 105. The needle is then pulled distally.

Figure 7:
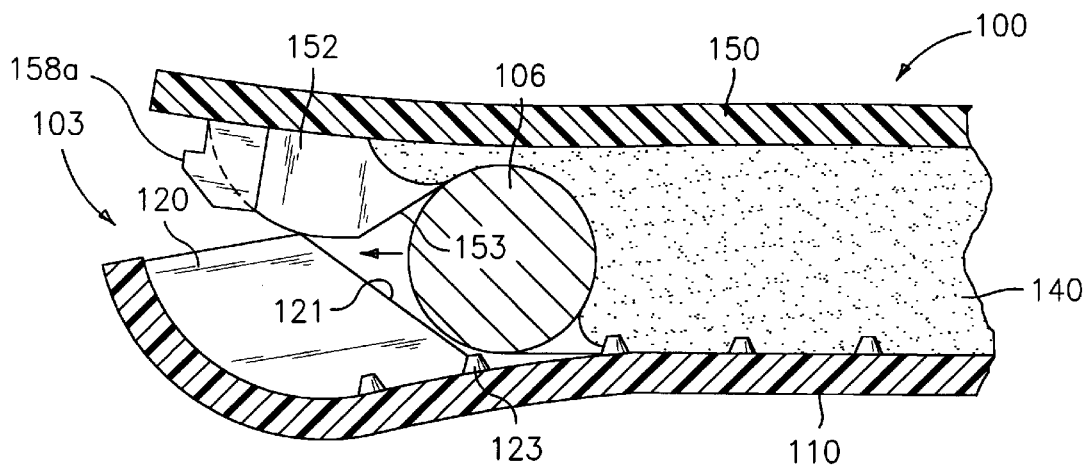
Figure 8:
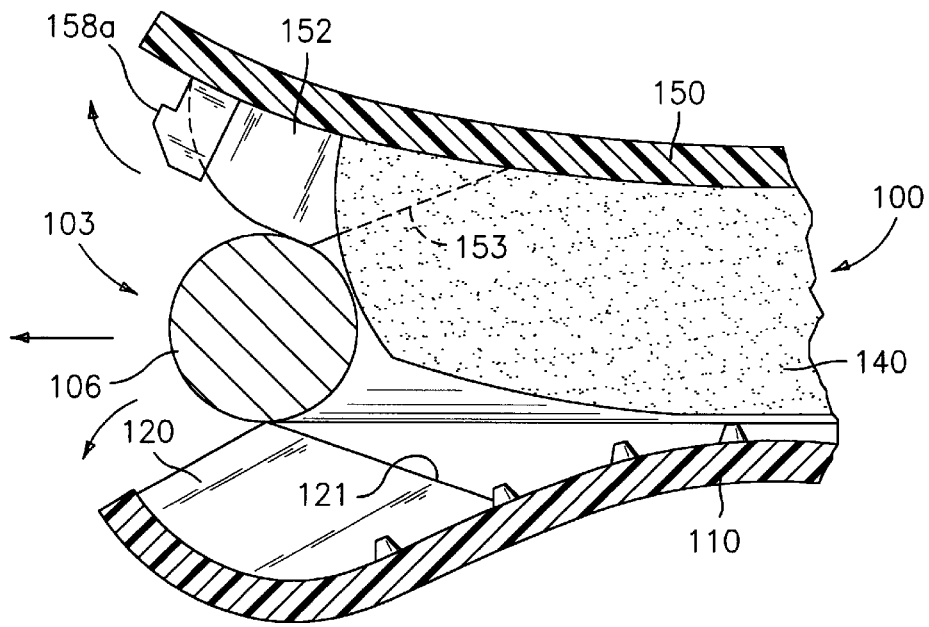

Referring to FIGS. 7 and 8, distal movement of the needle causes the needle to slidingly engage both camming surface 121 and 153, thereby biasing the distal edge of cover 150 upward and the distal edge of base 110 downward. Thus, latch 158a is disengaged from catch 118a and slot 117a, and the distal end 103 of the suture retainer package is cammed into an open configuration to permit removal of the needle 106 and suture 107 as shown in FIG. 8.

Figure 11:
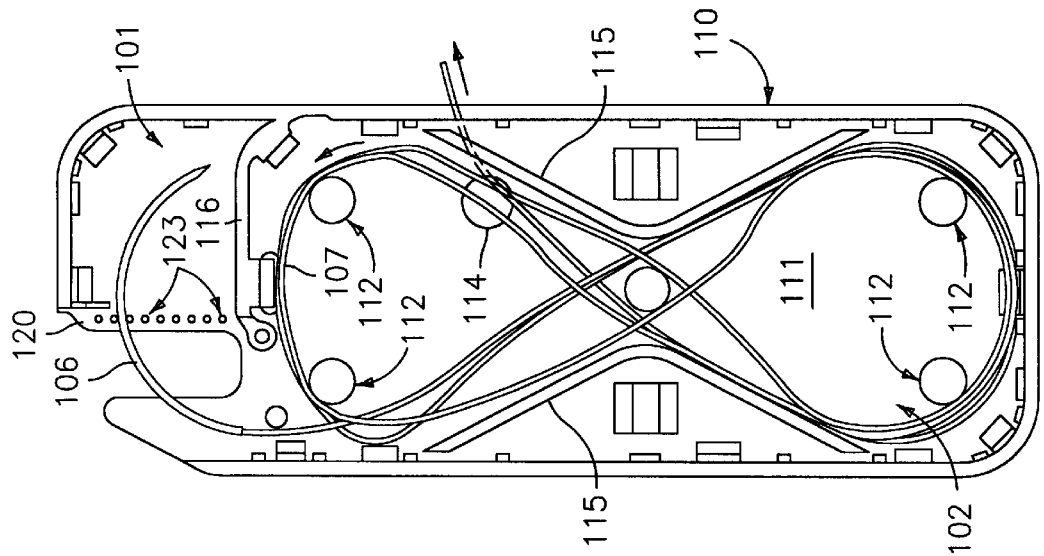
FIGS. 9, 10, and 11 are plan views illustrating a method for loading a needle suture combination into the suture retainer package; and, FIG. 12 is a perspective view showing the suture dispensing nozzle.
Figure 10:
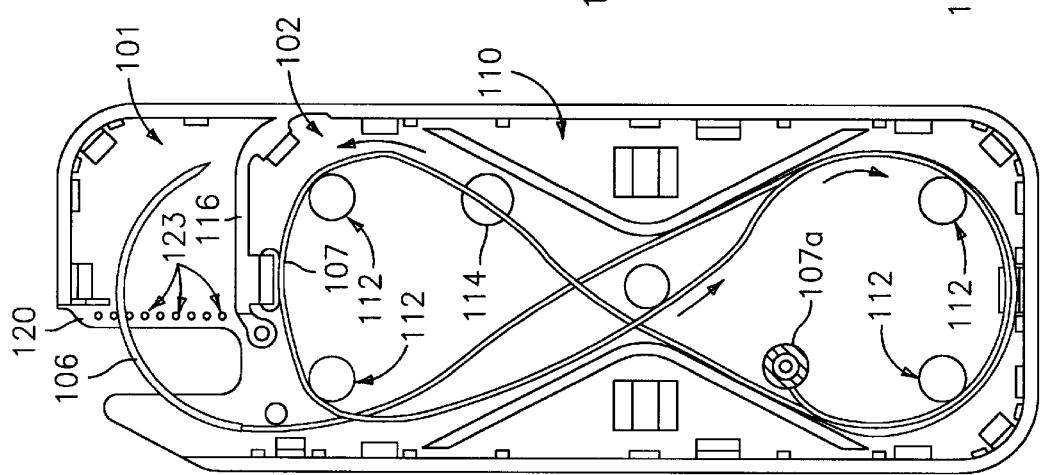
Figure 9:
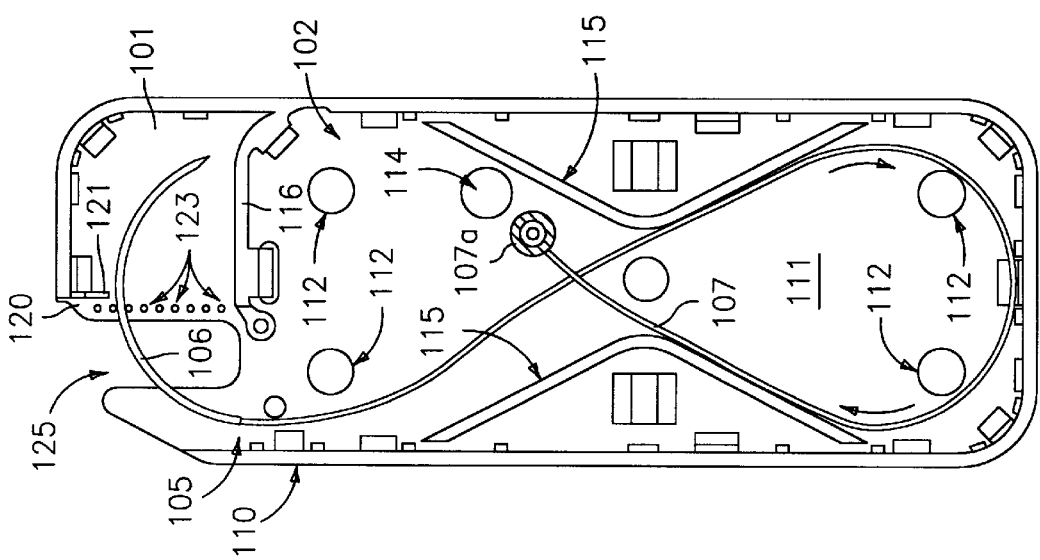
Figure 12:
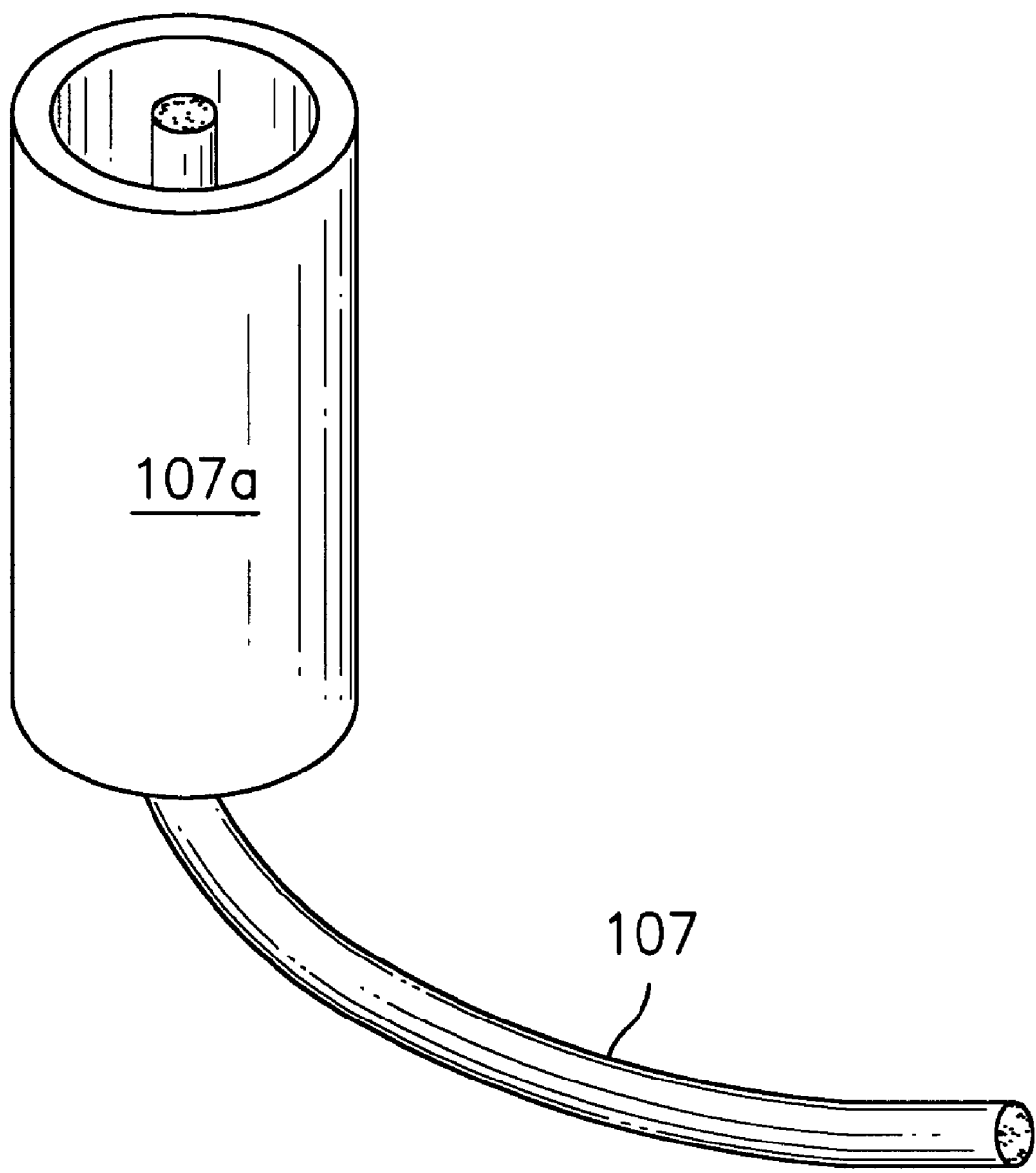

Referring now to FIG. 9, loading of the needle-suture combination 105 is accomplished by placing the needle 106 in a desired position along the row of indexing studs 123 within the needle storage compartment 101. The free end of suture 107 is wound into a coil, the coil being moved around the array of winding pins disposed through winding pin access apertures 112 so as to form a figure 8 shaped suture loop. Referring also now to FIG. 12, a preferred method of dispensing the suture 107 is by drawing it by vacuum into a straight or curved suture dispensing nozzle 107a, which can be a straight or curved tubular member. Nozzle 107a can be moved along a predetermined path with suture 107 being dispensed therefrom as nozzle 107a moves around the winding pins, thereby drawing out the suture 107. The suture loop is maintained in the figure 8 configuration at least partially by means of the V-shaped ridges 115. The suture 107 is laid down from the distal left corner of the suture storage compartment 102 to the proximal right corner of the suture storage compartment 102. The suture is then brought around winding pin apertures 112 in the vicinity of the proximal end of the base and up from the proximal left corner of the suture storage compartment 102 to the distal right corner of the suture storage compartment 102. Referring to FIGS. 10 and 11, the suture 107 is then brought around winding pin apertures 112 in the vicinity of the distal end of the suture storage compartment 102 and brought down again from the distal left corner of the suture storage compartment 102 to the proximal right corner of the suture storage compartment 102. This winding process is repeated until the entire length of suture has been drawn out of the nozzle 107a and laid down. Thereafter, the cover 150 can be joined to the base 110 by snap fit engagement of the latches 157 with the slots 117 and catches 118.

The suture retainer package 100 can then be inserted in an envelope (not shown) fabricated from a microbe-impervious material and hermetically sealed. The suture retainer package 100 and its contents can be sterilized after being sealed in the envelope by various methods such as gamma radiation and gaseous sterilization with steam or ethylene oxide. In the event that gaseous sterilization is employed at least part of the envelope should be fabricated from a porous microbe-impervious material such as TYVEK® brand spun bonded polyolefin sheet. Such methods of sterilization are known to those with skill in the art.

It will be understood that various modifications may be made to the embodiments described herein. Therefore the above description should not be construed as limiting, but merely as exemplifications of preferred embodiments. Those skilled in the art will envision other modifications within the scope and spirit of the claims appended hereto.

What is claimed is:

1. A method for loading a needle-suture combination into a package, comprising:
   a) providing at least one needle-suture combination;
   b) providing a needle-suture retaining package which includes a cover, and a base which is attachable to the cover so as to define an enclosure volume, the base having a planar surface and first and second V-shaped ridges projecting transversely from the plane of the surface and extending along the surface, each V-shaped ridge shaped ridge being in opposing relation to the vertex portion of the second V-shaped ridge so as to define a space therebetween having a constricted portion;
   c) positioning the needle in the base;
   d) positioning a major portion of the suture on the base in the space between the first and second V-shaped ridges; and
   e) attaching the cover to the base.

2. The method of claim 1 wherein the base includes a dividing ridge for defining a needle retaining compartment and a suture containing compartment, and said step of positioning the needle in the base comprises positioning the needle in the needle-retaining compartment.

3. The method of claim 1 wherein the base further includes a longitudinally oriented row of spaced apart indexing studs, and the step of positioning the needle in the base comprises positioning the needle between two of the studs.

4. The method of claim 3 wherein the base includes a longitudinally extending notch positioned in the vicinity of the row of indexing studs, and the step of positioning the needle in the base further comprises positioning the needle such that at least a portion of the needle extends laterally across the notch.

5. The method of claim 1 wherein the base includes winding pin access apertures and the method further includes the step of inserting winding pins through the winding pin access apertures.

6. The method of claim 5 wherein the step of laying the suture down comprises winding the suture around the winding pins.

7. The method of claim 1 wherein the step of laying the suture down includes laying the suture down to form a suture coil having generally figure 8 shaped loops.

8. The method of claim 1 wherein the step of laying the suture down includes dispensing the suture from a dispensing nozzle.

9. The method of claim 8 wherein the suture is releasably held in the dispensing nozzle by means of a vacuum.

10. The method of claim 1 wherein the step of attaching the cover to the base is accomplished by snap lock engagement.

11. The method of claim 1 further including the step of enclosing the loaded package in a sealed envelope.

12. The method of claim 11 further including the step of sterilizing the loaded package.

13. The method of claim 12 wherein the step of sterilizing is accomplished by subjecting the sealed envelope with the enclosed loaded package to gamma radiation.

14. The method of claim 12 wherein at least a portion of the envelope is fabricated from a microbe-impervious, porous sheet and the step of sterilizing is accomplished by subjecting the sealed envelope with the enclosed loaded package to ethylene oxide.

15. A method for loading a needle-suture combination into a package, comprising:
    a) providing at least one needle-suture combination;
    b) providing a needle-suture retaining package which includes a cover, and a base which is attachable to the cover so as to define an enclosure volume, the base having a planar surface and first and second V-shaped ridges projecting transversely from the plane of the surface and extending along the surface, each V-shaped ridge having a vertex portion, the vertex portion of the first V-shaped ridge being in opposing relation to the vertex portion of the second V-shaped ridge so as to define a space therebetween having a constricted portion;
    c) positioning the needle in the base;
    d) forming a suture coil having figure 8 shaped loops by positioning a major portion of the suture on the base in the space between the first and second V-shaped ridges; and
    e) attaching the cover to the base.

16. The method of claim 15 wherein the base further includes a longitudinally oriented row of spaced apart indexing studs, and the step of positioning the needle in the base comprises positioning the needle between two of the studs.

17. The method of claim 16 wherein the base includes a longitudinally extending notch positioned in the vicinity of the row of indexing studs, and the step of positioning the needle in the base further comprises positioning the needle such that at least a portion of the needle extends laterally across the notch.

18. The method of claim 15 wherein the base includes winding pin access apertures and the method further includes the step of inserting winding pins through the winding pin access apertures.

19. The method of claim 18 wherein the step of laying the suture down comprises winding the suture around the winding pins.

20. The method of claim 15 wherein the step of attaching the cover to the base is accomplished by snap lock engagement.

* * * * *